(12) United States Patent
Bouldin

(10) Patent No.: US 7,842,486 B2
(45) Date of Patent: Nov. 30, 2010

(54) PRODUCTION OF A FERMENTATION PRODUCT FROM A COMPOSITE MATERIAL

(75) Inventor: Floyd E. Bouldin, McMinnville, TN (US)

(73) Assignee: Bouldin Corporation, McMinnville, TN (US)

( * ) Notice: Subject to any disclaimer, the term of this patent is extended or adjusted under 35 U.S.C. 154(b) by 338 days.

(21) Appl. No.: 11/765,349

(22) Filed: Jun. 19, 2007
(Under 37 CFR 1.47)

(65) Prior Publication Data

US 2008/0108118 A1    May 8, 2008

Related U.S. Application Data

(60) Provisional application No. 60/814,927, filed on Jun. 19, 2006.

(51) Int. Cl.
*C12P 7/08* (2006.01)
(52) U.S. Cl. .................................................. 435/163
(58) Field of Classification Search .................. None
See application file for complete search history.

(56) References Cited

U.S. PATENT DOCUMENTS

| 1,490,162 | A | | 4/1924 | Dow ........................... 425/156 |
|---|---|---|---|---|
| 2,780,987 | A | | 2/1957 | Wall ............................ 100/249 |
| 3,564,993 | A | | 2/1971 | Tezuka et al. ................ 100/269 |
| 3,850,771 | A | | 11/1974 | Penque ........................ 264/187 |
| 3,858,504 | A | | 1/1975 | Boyer .......................... 100/215 |
| 4,099,457 | A | | 7/1978 | Hyden ......................... 100/215 |
| 4,110,281 | A | | 8/1978 | Dreer .......................... 523/129 |
| 4,153,404 | A | | 5/1979 | Ottman ........................ 425/352 |
| 4,357,214 | A | * | 11/1982 | La Mori et al. ................ 203/19 |
| 4,569,649 | A | | 2/1986 | Gross .......................... 425/432 |
| 4,729,304 | A | | 3/1988 | Gardella et al. ............. 100/218 |
| 4,772,430 | A | | 9/1988 | Sauda et al. ..................... 588/8 |
| 5,104,419 | A | | 4/1992 | Funk ............................. 48/209 |
| 5,135,861 | A | | 8/1992 | Pavilon ....................... 435/162 |
| 5,302,331 | A | | 4/1994 | Jenkins ....................... 264/115 |
| 5,363,758 | A | | 11/1994 | Wildes et al. ................ 100/215 |
| 5,427,650 | A | | 6/1995 | Holloway ........................ 162/5 |
| 5,932,456 | A | | 8/1999 | Van Draanen et al. ....... 435/144 |
| 6,017,475 | A | | 1/2000 | Cantrell ...................... 264/140 |
| 6,234,780 | B1 | | 5/2001 | Liu et al. ..................... 425/256 |
| 6,306,248 | B1 | | 10/2001 | Eley .............................. 162/4 |
| 6,397,492 | B1 | | 6/2002 | Malley ......................... 34/411 |
| 2004/0080072 | A1 | | 4/2004 | Bouldin et al. | |

* cited by examiner

*Primary Examiner*—Herbert J. Lilling
(74) *Attorney, Agent, or Firm*—Waddey & Patterson, P.C.; Ryan D. Levy; Edward D. Lanquist, Jr.

(57) ABSTRACT

A method of converting a composite material derived from municipal solid waste into alcohol is provided.

17 Claims, No Drawings

PRODUCTION OF A FERMENTATION PRODUCT FROM A COMPOSITE MATERIAL

CROSS-REFERENCES TO RELATED APPLICATIONS

This application is a application which claims benefit of Provisional Patent Application Ser. No. 60/814,927 filed Jun. 19, 2006, entitled "Production of a Fermentation Product from a Composite Material" which is hereby incorporated by reference.

BACKGROUND OF THE INVENTION

1. Technical Field

The present invention relates to a method of producing a fermentation product from a composite material. More particularly, the present invention relates to a method of producing ethanol from a composite material derived from municipal solid waste.

2. Background Art

By far the most common method of solid waste disposal in the United States is the landfill followed by incineration while composting of solid wastes accounts for only an insignificant amount.

In modern landfills, the refuse is spread in thin layers, each of which is compacted by heavy industrial equipment before the next layer is spread. When about ten feet of refuse has been deposited, it is covered by a thin layer of clean earth which also is compacted. Pollution of surface and groundwater is believed to be minimized by lining and contouring the fill, compacting and planting the cover, selecting proper soil, diverting upland drainage, and placing wastes in sites not subject to flooding or high groundwater levels.

Land-filling does pose many problems and concerns, including rising landfill maintenance and development costs, decreasing availability of landfill sites, and an increasing risk that substances leaching from landfills may contaminate groundwater and surface water. Landfills are also known to generate flammable gases through the anaerobic decomposition of the organic solid waste and thus proper venting and burning of the gases is often necessary to eliminate or alleviate potentially dangerous conditions.

Sanitary landfills were considered the cheapest most satisfactory means of disposal, but only if suitable land was available for use within an "economic range" of the source of the wastes (i.e., geographic proximity making waste removal and hauling economically feasible), because collection and transportation costs are known to account for seventy-five percent of the total cost of solid waste disposal and management.

A growing trend associated with the treatment and handling of solid waste material is "resource recovery". Resource recovery is intended to recover useful materials from raw municipal solid waste. The handling of such wastes may include preprocessing the municipal solid waste with grinding or shredding machines, magnetic separators, air classification that separates the light and heavy fractions, screening, and/or washing. Resource recovery methods, therefore, attempt to reduce (i.e., recycle) the solid waste into a more manageable, although not always useful form, but such methods are known to be quite costly.

One type resource recovery method is the conversion of waste into energy, either directly or indirectly. Historically, the most common conversion method of waste into energy has been the incineration of the waste material. However, this method of recovering energy is becoming less and less feasible due to both the cost and environmental constraints. Additionally, the increasing stringency of air emission standards as well as the public health concerns have influenced industry to create different technologies for the conversion of municipal waste into energy.

Other methods of waste-to-energy conversion including the preparation of a fuel source material from the waste product. For example, U.S. Pat. No. 5,135,861 issued to Pavilon, discloses the production of anhydrous ethyl alcohol from a quantity of biomass. The carbon dioxide acquired from the fermentation process of the biomass is utilized to hydrolyze additional biomass for fermentation into ethyl alcohol.

Draanen et al. (U.S. Pat. No. 5,932,456) claims a method of fermenting biomass to produce either ethanol or other fermentation products including citric acid and isopropanol. The '456 patent preferably uses the microorganism *Zymomonas mobilis* for the fermentation of biomass and solid waste and demolition debris.

U.S. Pat. No. 5,104,419, issued to Funk, describes a method of producing a liquid fuel such as methanol from a waste source such as solid municipal waste. The process includes partially oxidizing and combusting the solid waste material under high temperatures as well as gas separation techniques to produce a liquid fuel source from the waste material.

Most commonly the conversion of waste into energy is an indirect process wherein liquid ethanol is produced. Ethanol is a flammable, colorless chemical compound with the formula $C_2H_5OH$. Currently the largest single use of ethanol is for motor fuel and fuel additives. Thus far, the United States fuel ethanol industry is largely based on the fermentation of corn byproducts. With its current capacity well over 10 billion liters annually, the need for producing ethanol will continue to grow significantly as the Energy Policy Act of 2005 requires U.S. fuel ethanol production to increase to at least 7.5 billion gallons by the year 2012. Furthermore, ethanol is also used in the production of biodiesel so long as the ethanol has a water content of less than 2%. The ethanol replaces the much more toxic alcohol, methanol, providing for a safer way to produce biodiesel.

In addition to the fuel industry, ethanol is also used in the production of other chemical compounds such as ethylene and butadiene. Even further, ethanol can be used to make ethylamines which are commonly used in the synthesis of pharmaceutical compounds.

Until now, drawbacks associated with the conversion of waste materials to energy have included the inconsistency of the starting material as well as the achievement of a conversion rate of municipal solid waste to energy which is economically feasible.

It is believed that a specific composite material will remedy these concerns while providing for a sufficient conversion rate to a liquid fuel.

The composite material and art to which the inventive process relates include the information of the type disclosed in U.S. Pat. No. 6,017,475 granted to Cantrell and also U.S. Patent Application No. 2004/0080072 of Bouldin et al. which are incorporated by reference and are fully set forth herein. Notably, the '072 application is directed to a process of deriving a composite material from municipal solid waste.

What is desired, therefore, is a method for efficiently making ethanol from a composite material derived from municipal solid waste wherein the overall conversion from waste to ethanol is sufficiently efficient and also economically viable.

SUMMARY OF THE INVENTION

The present invention provides a method uniquely capable of transforming a composite material derived from municipal solid waste into ethanol. The inventive process is able to reach a conversion rate of the composite material to ethanol of over 60%. In addition, the conversion process of the composite material to ethanol is to be linked to the initial formation of the composite material. Furthermore, the novel method allows for the use of a multitude of fermentation components including a variety of fermenting microorganisms as well as system processing perimeters so that the conversion of the composite material to ethanol can be readily tailored.

More particularly, the inventive process uses fermentation techniques as the means for converting the composite material into an alcohol product, most often being ethanol.

An important characteristic for the fermentation of the composite material is the specific organic makeup of the composite material which will be fermented. For fermentation applications such as this, an abundance of simple carbohydrates more readily allows for the higher conversion rate of a composite material into ethanol. The inventive process allows for a conversion rate of the composite material to ethanol of from about 60% to an upper limit of about 90%.

The inventive process should include fermentation components in combination with their composite material to provide the necessary conditions for the high conversion rate of the composite material into ethanol. In addition, system parameters such as pH and temperature should be monitored and controlled so that the fermenting microorganism is most productive in converting the composite material into ethanol.

More specifically, the composite material derived from municipal waste should have a glucan weight percent of from about 25% to about 45%; a xylan weight percent of from about 1% to about 12%; and a mannan weight percent of from about 0% to about 2% to supply the fermenting microorganism with sufficient carbohydrates with the conversion.

Additionally, the fermentation of the composite material to ethanol can be configured for a variety of reactor setups. This includes a batch operation, semi-batch operation, and also the capacity for running the fermentation process in a continuous manner.

Advantageously, municipal solid waste is ultimately converted into a useful energy source by deriving the composite material from the municipal solid waste, and subsequently fermenting the composite material under conditions allowing for a high conversion rate of the composite material into ethanol.

An object of the invention, therefore, is a process having characteristics for creating a fermentation product from a composite material.

Another object of the invention is a process in which a composite material derived from municipal solid waste is subsequently fermented to produce liquid ethanol.

Still another object of the invention is a method for creating ethanol from a composite material immediately subsequent to the creation of the composite material from the municipal solid waste.

Yet another object of the invention is a continuous conversion of the composite material into liquid ethanol.

Another object of the invention is the fermentation of the composite material wherein the conversion rate of the composite material into ethanol is of from about 60% to about 90%.

Even another object of the invention is the simultaneous saccharification and fermentation of the composite material.

In these aspects and others that will become apparent to the artist and upon review of the following description can be accomplished by subjecting a quantity of a composite material derived from municipal solid waste to a fermenting environment where a fermenting organism is under conditions to convert the composite material into ethanol. The inventive process should supply a composite material with the physical makeup of from about 25% to about 45% by weight glucan; of from about 1% to about 12% by weight xylan; and of from about 0% to about 2% by weight mannan so that a conversion rate of from about 60% to about 90% composite material to ethanol can be achieved.

The inventive process may also advantageously remove organic materials from the composite material during the conversion to ethanol while leaving behind other useful material such as scrap plastic and metals.

The ethanol recovered from the inventive process can be subsequently removed from the combination of the composite material and fermentation components by distillation or processing. Furthermore, the fermentation components used for processing may be recycled for additional fermentation of fresh composite material.

It is to be understood that both the foregoing general description and the following detailed description provide embodiments of the invention and are intended to provide an overview of framework of understanding to nature and character of the invention as it is claimed.

DETAILED DESCRIPTION OF THE INVENTION

Solid municipal waste can generally be described as comprising: 1) garbage including decomposable waste from food; 2) rubbish including combustible decomposable waste such as paper, wood, and cloth, or non-combustible decomposable waste such as metal, glass, and ceramics; 3) ashes including the residue of the combustion of solid fuels; 4) large waste including demolition and construction debris and trees; 5) sewage treatment solids including the material retained on sewage treatment screens, subtle solids, and biomass sludge; 6) industrial waste including chemicals, paint, and sand; 7) mining waste including coal refuse piles; and 8) agricultural waste including farm animal manure and crop residues. Specifically, municipal solid waste includes both garbage and also rubbish. Both garbage and rubbish of a municipal solid waste can undergo a preprocessing step wherein the municipal solid waste is shredded, ground, and if necessary, dewatered prior to insertion into a hydrolyzer for the actual processing steps to convert municipal solid waste to a composite material.

The preferred pre-processing portion of the process of converting municipal solid waste into a composite material preferably includes at least one grinder, at least one shredder, and any other necessary material reduction apparatus used to reduce the particle size of the municipal solid waste into a more useful particle size.

Optionally, the shredded and ground municipal solid waste can be transferred either automatically or manually to a dewatering press in order to uniformly hydrate the material prior to introducing the municipal solid waste into a hydrolyzer.

The hydrolyzer may be of the type which includes an outer containment vessel having an exterior jacket and an interior pressure vessel with an air space situated between the interior vessel and the jacket. A heated steam inlet and exit may also be attached to the jacket and communicate with the air space. When the preprocess municipal solid waste is introduced into the interior of the hydrolyzer pressure vessel, the operator can introduce heated steam into the air space surrounding the interior vessel to heat the interior vessel and the preprocessed municipal solid waste. Furthermore, preheating of the vessel jacket by introducing a steam therein prior to introducing the municipal solid waste into the hydrolyzer is also acceptable.

A preferred temperature of the steam in the outer jacket is 350° F. Notably the process of producing the composite material could be carried out at other temperatures and pressures within permissible ranges but the associated time for completion of the production of the composite material at other than the preferred temperature and pressure will vary. As known in the art, the greater the temperature and pressure in a hydrolyzer, the faster the chemical reactions will generally occur. However, a practical efficient maximum temperature and pressure also exist.

The pressure and temperature in conjunction with the preprocessed municipal solid waste act as to speed the chemical reaction of the decomposition of the municipal solid waste within the vessel. This high temperature and pressure environment causes the municipal solid waste to rapidly decompose into its basic constituent elements and allows them to recombine or remain in their organic cellulose form.

After the allotted time within the hydrolyzer has elapsed, the composite material exits the hydrolyzer. This composite material is known as fluff and is a mixture of cellulose fibers and other elements present in the material prior to processing. The fluff can then be dried and used in a variety of applications.

A more detailed description of the process equipment for producing fluff is in Bouldin et al., U.S. patent application Ser. No. 10/545,144 entitled "Apparatus and Method for Transforming Solid Waste into Useful Products" which is hereby incorporated by reference.

In the practice of the present invention, fluff is generally considered a very heterogeneous mixture of shredded materials consistent of potentially cellulosic fibers mixed with small pieces of metal foil, hard plastics, rubber strips, and fabric. Debris that is clearly noncellulosic is preferably removed from the fluff prior to the start of the fermentation process. Debris cleaned fluff contains from about 10% moisture content to about 20% moisture content. The main organic constituents of fluff are glucan, xylan, and mannan, wherein glucan is present of from about 25% to about 45% by weight; xylan is present of from about 1% to about 12% by weight; and mannan is present of from about 0% to about 2% by weight. Glucan, xylan, and mannan are all types of carbohydrates of which different organisms may metabolize and produce ethanol.

Glucans are molecules comprised of glucose monomers linked together by glycosidic bonds to form a polysaccharide. Of particular note is the glucan cellulose, which is a relatively long chain polysaccharide. Xlyan is a polysaccharide composed of xylose which is a five-carbon sugar and includes an aldehyde functional group. Xylose is typically found in edible plants and is considered an important nutritional carbohydrate for human beings. Mannan, the smallest percentage polysaccharide present in fluff, consists of mannose sugars. Mannose is a six carbon sugar found in certain fruits.

These organic components may be fermented by a variety of organisms wherein the organic components are metabolized in the absence of oxygen to produce ethanol and carbon dioxide. As known in the art of fermentation, *Saccharomyces cereuisiae* is the standard species of yeast which can metabolize glucose in the absence of oxygen to produce ethanol. A variety of other fermentation organisms may be utilized to convert fluff into ethanol including a variety of recombinant bacteria and archaea as well as wild-type yeast and recombinant yeast strands. Recombinant organisms include bacteria, archaea, yeast, and fungi which have been engineered to include non-native genetic material in order to create a pathway for the conversion of fluff to ethanol. This may include the incorporation of genetic material coding for the enzyme alcohol dehydrogenase into the organism. Preferred fermentation organisms for the conversion of fluff to ethanol includes *Saccharomyces cereuisiae, Zymomonas mobilis*, and well as engineered strains of either organism. Additionally, engineered *Escherichia coli* can also be utilized for metabolizing fluff to ethanol.

In order to commence the fermentation of fluff, the fluff should first be broken down from its cellulose-type structure into sugars which can be fermented by the selected organism. Typically this may involve the hydrolysis of the cellulose material into its sugar components. Hydrolysis materials for the conversion of fluff to ethanol include any materials which will hydrolyze glucan, zylan, and mannan into the monomer sugars of glucose, zylose, and mannose. Other hydrolyzing materials include, but are not limited to solutions of sulfuric acid which have proven efficient at hydrolyzing carbohydrate materials.

In a preferred embodiment, the fluff to ethanol conversion comprises a simultaneous saccharification and fermentation process wherein the fluff is broken down to fermentable components and simultaneously fermented into ethanol. Typically the rate controlling step is the hydrolysis of fluff allowing for the computation of reasonably simple fermentation kinetics in determining the production of ethanol.

In one embodiment, a solution of sulfuric acid in a concentration of from about 50% to about 90% of sulfuric acid to water is utilized to hydrolyze the fluff into fermentable materials. Furthermore, in a preferred embodiment, the fluff may be broken down by digestive enzymes such as beta glucosidase and also cellulase. Typical concentrations of beta glucosidase are of from about 15 units per gram cellulose to about 60 units per gram cellulose, whereas cellulase may be added of from about 5 units per gram cellulose to about 25 units per gram cellulose.

Simultaneous with the addition of the digestive enzymes is the inoculation with a fermenting organism. Other fermentation components can include the addition of nutrients for the fermenting organism so that the production of ethanol from fluff is maximized. This can include such additives as corn steep liquor in a preferred 3% solution in deionized water. Other nutritional supplements for the fermenting organisms can include magnesium which is known in the art to prolong a microorganism's exponential growth while also reducing the decline in ethanol production upon the conclusion of batch fermentations.

The total fermentation time for the simultaneous saccharification and fermentation is of from about 40 hours to about 100 hours with the preferable time for batch fermentation preferably at about 50 hours. The temperature of the fermentation chamber is typically from about 25° C. to about 40° C. with the temperature preferably at about 37° C. for when *Saccharomyces cereuisiae* is utilized as the fermentation organism. Furthermore, this temperature range could either be significantly lower or significantly greater depending on the choice of fermentation organisms, wherein, for example, a choice of a hyperthermophile would require a fermentation temperature of around at least 85° C.

The simultaneous saccharification and fermentation can be run in a variety of process arrangements. One such reactive setup is a batch reactor design where a fermentation reactor is initially charged with the fluff and fermentation components and subsequently the entire fermentation reactor is brought to the desired fermentation conditions including desired temperature and left for the fermentation reaction to proceed. The conversion of fluff to ethanol may also be operated in a semi-batch reactor design where liquid containing a substantial fraction of ethanol is continuously withdrawn from the reactor while fluff and necessary fermentation components are continuously added to the reactor. Yet furthermore, a continuous reactor design is an open system of fermenting the fluff to ethanol in which all components are continuously added and removed from the fermentation reactor.

Through the inventive process of creating ethanol from fluff, a conversion rate of from about 60% to about 90% of the theoretical rate can be achieved. In a preferred embodiment, maximum conversion of fluff into ethanol is achieved at from about 45 hours to about 100 hours. The remaining solid, unfermented components of fluff are typically composed of fiber scraps, non-removed metal scraps, and synthetic fibers.

In order to further illustrate the principles and operation of the present invention, the following example is provided. However, this example should not be taken as limiting in any regard.

EXAMPLE

Fluff is received and stored in sealed plastic bags at 4° C. Sub-samples are oven dried at 105° C. overnight to determine moisture content and to prepare samples for quantitative saccharification.

Samples for quantitative saccharification are first cleaned of metallic, plastic, and rubbery debris, then are milled in a coffee grinder to reduce the particle size of organic material. Triplicate 0.300 g samples are placed in 15-mL glass test tubes along with 3.00 mL of 72% $H_2SO_4$.

The mixtures are placed in a 30° C. shaking water-bath for 60 minutes and are stirred every 10 minutes to insure adequate contact between acid and sample. After 60 minutes, the samples are transferred to 150-mL culture bottles, diluted with 84 mL of deionizer water, and are capped and placed in an autoclave at 121° C. for another 60 minutes. Sub-samples of the final acid hydrolysates are centrifuged, neutralized with $CaCO_3$ and are analyzed by HPLC (BioRad P-column) with refractive index detection.

Results from the quantitative saccharification are used to determine the glucan (cellulose) loading for the subsequent simultaneous saccarification and fermentation. Two sets of duplicate culture bottles (250-mL) are loaded with air-dried fluff containing 2.00 g glucan. Debris is removed from all samples before weighing, with one set having the debris added back. A solution of 3% corn seep liquor in deionized water containing 5 mM magnesium is added to the fluff samples which are subsequently capped, purged with $CO_2$, and are autoclaved at 121° C. for 60 minutes. Samples are cooled to 37° C. before inoculation with *Saccharomyces cereuisiae* $D_5A$, cultured overnight in YPD broth. Both Cellulase and β-glucosidase enzymes are added (15 units/g and 45 units/g cellulose respectively) and the bottles are incubated at 37° C. on a rotary shaker for 96 hours. Samples for ethanol analyses are withdrawn at 10, 24, 49, 74 and 96 hours, acidified with dilute $H_2SO_4$, filtered and stored at 4° C. until HPLC analysis (BioRad H-column) with refractive index detection is performed.

The analysis shows fluff to be a heterogeneous mixture of shredded materials consisting of potentially cellulosic fibers mixed with small pieces of metal foil, hard plastic, rubbery strips, and fabric. Debris that is clearly non-cellulosic accounted for about 7% of the air-dried sample. This is removed before weighing samples. The cleaned fluff is about 15.3% moisture with about 7% by weight of clearly non-cellulosic debris removed prior to the quantitative saccharification. Results of the quantitative saccharification are: 34.0% glucan, 4.2% xylan and 0.3% mannan.

The simultaneous saccharification and fermentation results for the sets of fluff with and without debris are comparable, so final results are reported as averages of both sets. Ethanol production (g/L) at 10, 24, 49, 74 and 96 hours is about: 4.28, 5.82, 8.4, 8.3, 8.41. The final quantity of ethanol represents a conversion rate of 82.5% of theoretical.

As illustrated above, the inventive process of fermenting fluff can produce significant amounts of ethanol by way of a simplified fermentation system. Moreover, the example is representative of the ability to produce large quantities of ethanol utilizing a highly economical substrate. Furthermore, the process is both economical and greatly beneficial for ethanol used in fuel production while decreasing the presence of municipal solid waste which would otherwise occupy landfill space.

Accordingly, by the practice of the present invention, ethanol is produced from a composite material derived from a municipal solid waste. The method produces a substantially large quantity of ethanol in an economical fashion from a material which would otherwise occupy landfill space.

The disclosures of all cited patents and publications referred to in this application are incorporated herein by reference.

The above description is intended to enable the person skilled in the art to practice the invention. It is not intended to detail all of the possible variations and modifications that will become apparent to the skilled worker upon reading the description. It is intended, however, that all such modifications and variations be included within the scope of the invention that is defined by the following claims. The claims are intended to cover the indicated elements and steps in any arrangement or sequence that is effective to meet the objectives intended for the invention, unless the context specifically indicates the contrary.

What is claimed is:

1. A method for producing an alcoholic fermentation product comprising:
    a) providing a quantity of municipal solid waste;
    b) preprocessing the municipal solid waste to create preprocessed municipal solid waste having a more useful particle size;
    c) inserting the preprocessed municipal solid waste into a hydrolyzer;
    d) processing the municipal solid waste within the hydrolyzer to create a composite material containing glucan, xylan and about at least 10 percent moisture content; and
    e) treating the composite material with simultaneous saccharification and fermentation components to convert at least a portion of the composite material to an alcoholic fermentation product having at least about 60 percent alcohol.

2. The method of claim 1 further comprising removing a majority of the inorganic debris of the composite material of step d) prior to step e).

3. The method of claim 1 further comprising milling the composite material of step d) prior to step e).

4. The method of claim 1 wherein the composite material of step e) contains from about 25% to about 45% by weight glucan, and from about 1% to about 12% xylan, and from about 0% to about 2% by weight mannan.

5. The method of claim 1 wherein the composite material of step e) contains from about 10% moisture content to about 20% moisture content.

6. The method of claim 1 wherein the fermentation product is ethanol.

7. The method of claim 6 wherein the conversion rate of the composite material of step e) to ethanol is of from about 60% to about 90%.

8. The method of claim 1 wherein the fermentation components include at least one fermentation organism.

9. The method of claim 8 wherein the fermentation organism is Saccharomyces cervisiae.

10. The method of claim 1 wherein the fermentation components include at least one digestive enzyme.

11. The method of claim 10 wherein the digestive enzyme is beta-glucosidase.

12. The method of claim 10 wherein the digestive enzyme is cellulase.

13. The method of claim 1 wherein the treatment of step e) is of from about forty hours to about 100 hours.

14. The method of claim 1 wherein the treatment of step e) is at from about 25° C. to about 40° C.

15. The method of claim 1 wherein step e) is operated as a batch process.

16. The method of claim 1 wherein step e) is operated as a semi-batch process.

17. The method of claim 1 wherein step e) is operated as a continuous process.

\* \* \* \* \*